(12) United States Patent
Riazanskaia et al.

(10) Patent No.: US 8,096,199 B2
(45) Date of Patent: Jan. 17, 2012

(54) SAMPLER AND METHOD OF SAMPLING

(75) Inventors: Svetlana Riazanskaia, Manchester (GB); Charles Laurence Paul Thomas, Leicestershire (GB)

(73) Assignee: Conopco Inc., Englewood Cliffs, NJ (US)

( * ) Notice: Subject to any disclaimer, the term of this patent is extended or adjusted under 35 U.S.C. 154(b) by 1014 days.

(21) Appl. No.: 12/069,254

(22) Filed: Feb. 8, 2008

(65) Prior Publication Data
US 2008/0190218 A1   Aug. 14, 2008

(30) Foreign Application Priority Data
Feb. 10, 2007   (GB) .................................. 0702592.7

(51) Int. Cl.
    *G01N 1/00*   (2006.01)
(52) U.S. Cl. ...................................... 73/864.33
(58) Field of Classification Search ................ 73/864.31
    See application file for complete search history.

(56) References Cited

U.S. PATENT DOCUMENTS

| | | | | |
|---|---|---|---|---|
| 2,771,776 A | * | 11/1956 | Haven ........................ | 73/864.33 |
| 3,065,637 A | * | 11/1962 | Landes ....................... | 73/863.31 |
| 3,748,905 A | * | 7/1973 | Fletcher et al. ............. | 73/863.25 |
| 4,577,490 A | * | 3/1986 | Bray et al. ...................... | 73/40.7 |
| 4,754,655 A | | 7/1988 | Parker, III et al. .......... | 73/864.44 |
| 5,211,062 A | * | 5/1993 | Moser ........................ | 73/864.33 |
| 5,718,887 A | | 2/1998 | Wolf et al. ...................... | 424/65 |
| 5,939,647 A | * | 8/1999 | Chinn et al. ................ | 73/864.71 |
| 6,408,701 B1 | * | 6/2002 | Fujita ........................ | 73/864.71 |
| 7,010,991 B2 | * | 3/2006 | Lutz et al. .................. | 73/864.33 |
| 7,100,461 B2 | * | 9/2006 | Bradley et al. ............. | 73/864.33 |

FOREIGN PATENT DOCUMENTS

| | | |
|---|---|---|
| CA | 2244498 | 2/1999 |
| DE | 100 49 232 | 4/2002 |
| DE | 103 10 311 | 9/2004 |
| EP | 0 458 622 | 11/1991 |
| GB | 1 343 156 | 1/1974 |
| JP | 2003 021582 | 1/2003 |
| JP | 2004 226336 | 8/2004 |
| JP | 2004 294328 | 10/2004 |
| WO | 97/48373 | 12/1997 |

OTHER PUBLICATIONS

GB Search Report in a GB application GB 0702592.7.
PCT International Search Report in PCT application PCT/EP2008/051465.

* cited by examiner

*Primary Examiner* — Robert Raevis
(74) *Attorney, Agent, or Firm* — Karen E. Klumas

(57) ABSTRACT

A volatilizable substance can be sampled from a surface using a hand-held sampler employing a probe that comprises a supply tube in fluid communication with a pressurized gas supply and an outlet proximate to a target surface, a recovery tube having an inlet proximate to the target surface and being in fluid communication with a collector or analyzer and a skirt of varied depth. The probe is brought into contact with the surface, preferably in at least three points, gas flows out through the supply tube onto the surface, the volatilizable substance is volatilized, uptaken in to the gas and a fraction of the gas flows back through the recovery tube to the collector or analyzer, the remainder flowing under the skirt to prevent ingress of contaminants.

8 Claims, 4 Drawing Sheets

SAMPLER AND METHOD OF SAMPLING

The present invention relates to a device and particularly a hand-held device for sampling, a method for sampling from a surface, and the use of such a device and method to assess the efficacy of a treatment. The invention particularly employs a hydrodynamic gas flow.

Sampling volatilisable substances at a body surface can be inherently beneficial, in that it can be used to identify whether and/or which desirable or undesirable substances are present, and by taking a series of samples over time, changes in the concentration of such substances can be tracked. Thus, for example, the increase over time of malodorous substances on the body, eg in the underarm, can be monitored. Similarly, where a treatment to a body results in the presence or removal of a volatilisable substance on or from its surface, the efficacy of that treatment can be determined.

Methods and devices for sampling from bulk materials, be they gaseous, liquid or particulate solids are commercially available and commonly comprise a element that enters the bulk material, isolates a sample, possibly under reduced pressure, and thereafter transfers the isolated sample to an intermediate store or directly to an analyser. However, a similar device and method for sampling volatalisible substances from a surface such as human skin is not commercially available, as far as the inventors are aware.

Sampling a volatilisable substance from a surface poses a number of difficulties. First of all, there is a potentially significant problem of contamination as a result of the surface commonly being in contact with the atmosphere and/or clothing, and air contains not only many different contaminants, be they chemical or biological, and they can be in the form of gases, or suspended droplets or particulates. Likewise clothing can be contaminated by fluids or particulates that can be transferred onto the skin surface. Such contaminants not only constitute a problem as such, but there can be no guarantee that the levels of contamination remain constant, and indeed, they could be expected to change over time and between even adjacent volumes of air. Accordingly, there is a great risk of variable and inaccurate information being obtained. Likewise, if there is an interaction between the air and the substance to be sampled, there is a risk of a variable interaction, depending on how the air itself varies.

Secondly, there can be difficulties of reproducibility, depending on variation in the spacial relationship of the sampler and the sample surface. This may pose greater difficulties for some surfaces such as skin.

Various past methods of sampling substances from a target surface such as skin have included contacting the surface with a strip of absorbent material. Covering certain surfaces, such as skin can alter the characteristics of the surface compared with if the strip were absent, potentially distorting the result, and it would be desirable to find a method that could be targeted to a narrower region of the surface than is commonly available with strip sampling.

DE 10004932 discloses a device for sampling gas from within a furnace by pumping gas out of the furnace, passing it through an analyser and returning the gas to the interior of the furnace. This does not directly address the problems of analysing volatile substances from a surface.

JP 2004-226336 discloses a device for analysing volatile substances desorbed from a proximate surface of a semiconductor wafer. This device includes a probe that sits on the target wafer surface and forms with it a closed chamber. Whilst this might be suitable for analysing substances from a semi-conductor wafer, it not suitable for surfaces in general, and particularly for skin, because semi-conductor wafers are made and tested in extremely tightly controlled environments, all contaminants being removed to a very high level. In the outside world, contamination abounds.

DE 10310311 discloses a large scale device for sampling materials from the environment that is intended to be mounted on transport means, such as skids, a wheeled vehicle, a crawler type vehicle or a walking mechanism, that moves the device across a surface. Air from the environment is pumped towards the earth, and is sucked back through a central tube to an analyser, where it is compared with bypass air. Whilst this might be suitable on a large scale where changes in contamination of influent air can be averaged over a period of time, it is not desirable for small scale employment where contamination needs to be avoided and where it is often more practical to store a sample for subsequent analysis rather than compare two gas streams instantly.

OBJECT OF THE PRESENT INVENTION

It is an object of the present invention in one aspect thereof to devise a sampler for volatilisable substances which overcomes or ameliorates one or more of the problems identified above.

It is a further object of certain embodiments of the present invention to devise a sampler for sampling a volatilisable substance from a skin surface.

It is a still further object of some or other embodiments of the present invention to measure changes in concentration of a volatisable substance using a sampler of the first aspect.

It is a yet further object in a further aspect of the present invention to employ a sampler in accordance with the first aspect to assess the efficacy of a treatment to a surface.

BRIEF SUMMARY OF THE PRESENT INVENTION

According to a first aspect of the present invention, there is provided a sampler employing a hydrodynamic gas flow to volatilise substances from a surface and convey such substances to a collector or analyzer. A sampler for sampling of a volatilisable substance from an adjacent surface in accordance with the first aspect comprises a pressurised uncontaminated gas supply, a probe in fluid communication with the gas supply and with a collector or analyser, in which the probe and/or collector is capable of being hand held and the probe comprises a supply tube, a recovery tube and a skirt, the supply tube having an outlet at one end of the probe positioned to be able to direct a stream of gas under pressure from the gas supply onto the adjacent surface, the recovery tube having an inlet that is adjacent to the supply tube outlet and proximate to the surface and is in fluid communication with the collector or analyser, and the skirt is of varied depth around its periphery, extending beneath and surrounding both the supply tube outlet and recovery tube inlet, and has a tip enabling contact to be made with said adjacent surface whilst permitting a fraction of the gas to flow outwardly beneath the skirt.

In accordance with a second aspect of the present invention there is provided a method for sampling a volatilisable substance employing a sampler in accordance with the first aspect.

By virtue of the provision of such a sampler, the probe can be brought into contact with the surface such as skin, so that the skirt spaces the recovery tube inlet/supply tube outlet at predetermined distance from the surface, thereby minimising variability. The varied depth of the skirt, at least a fraction of which extends beneath the lower of the recovery tube inlet/ supply tube outlet means that only a fraction of the gas flowing out of the supply tube flows into the recovery tube, and the remainder flows outwardly beneath the skirt, thereby purging the surface and preventing the ingress of contaminants.

In determining the geometry of the sampler according to the present invention, upward is away from the recovery tube inlet towards the collector, outward is from the interior of the skirt radially towards the exterior, and in use, the supply tube outlet and recovery tube inlet of the probe are considered to be vicinal to and above the surface being sampled.

DETAILED DESCRIPTION AND PREFERRED EMBODIMENTS

The present invention relates to a sampler comprising a gas supply coupled to a probe that comprises a supply tube a recovery tube and a skirt, and a collector and brought into contact at its tip with a surface, such as a skin surface, the carrier gas being expelled under pressure through one of the tubes onto the surface and recovered through the second tube to the collector, the probe and/or collector being capable of being held in the hand.

The holding means for the probe and/or collector can comprise a handle attached thereto, or preferably may comprise the probe and/or collector itself, that separately or together are dimensioned to permit it or the two together to be grasped within a representative adult human hand. Such a hand herein is considered to have an overall finger plus palm length of 18 cm including a finger length of 8 cm and a palm width of 9 cm. Advantageously, said holding means comprises a zone in length of at least 8 cm, preferably at least 10 cm, desirably of up to 30 cm and in many embodiments up to 15 cm. The transverse circumference of the holding means is commonly up to 15 cm, desirably up to 10 cm and in many desirable embodiments at least 1 cm. An especially suitable range for the zone is from 1.5 to 5 or 7 cm in circumference. In one especially desirable configuration, the collector is mounted directly above and axially in line with the probe, and the probe and collector together resemble a pen, by which is meant a cylindrical body of dimensions suitable for grasping and direction by thumb, index and middle fingers and having one end for contact with a surface.

The probe terminates in said skirt in the vicinity of and surrounding the recovery tube inlet and supply tube outlet. The skirt in use not only functionally spaces the recovery tube from the surface at a predetermined distance, but additionally permits gas to purge contaminants proximate to the surface from beneath the probe. The depth of the skirt is not constant around its periphery, but is varied so as to provide a tip and preferably at least three tip locations around the periphery. Three tip locations or more such as four, and especially if they are well spaced around the periphery, for example symmetrically spaced or spaced at an angle to an adjacent tip of at least 360/(n+1) degrees, where n is the number of tips, stabilise the probe on the surface and minimise the risk of tilting or otherwise altering the distance between the surface and the recovery tube inlet or alter the path of gas flow from supply tube outlet to recovery tube inlet. The tip locations desirably permit the skirt to stand upright.

The skirt profile is at the discretion of the device maker, provided that it has a varied depth around its periphery, thereby providing a narrow gap through which a fraction of the gas can pass. The skirt is usually oriented perpendicularly to the surface. It can be mathematically continuous, such as serpentine, or discontinuous, such as castellated or comprise a plurality of downward prongs. The maximum depth of the skirt is, in practice, usually not greater than 5 mm, commonly up to 2 mm and in various preferred embodiments in the region of 1 mm below the recovery tube inlet. The extent of variation in its depth, i.e. defining the narrow gap, is often in the range of at least 0.1 mm, commonly not greater than 1 mm and in certain preferred embodiments up to 0.5 mm.

The variation in the skirt depth around its periphery enables a fraction of the volatilising gas to pass outwardly underneath the skirt to prevent ingress of external contamination. Often, the fraction of gas egressing beneath the skirt is at least 10% and can be at least 20%. The fraction of gas so egressing is usually less than 80% and commonly less than ⅔rds.

The supply tube terminates at one end within the skirt in a gas outlet oriented to direct the gas towards and/or across the target surface, enabling the gas to contact the surface and volatilise substances therefrom. Advantageously, the supply tube in the vicinity of its outlet is orientated to direct the gas at an angle of at least 45 degrees relative to the plane of the target surface and particularly in some preferred embodiments within 10 degrees from the vertical to the surface plane. Advantageously, the skirt and the supply tube have a common axis or parallel axes, and preferably are coaxial. The outlet shape is at the discretion of the maker. It is advantageously for the supply tube outlet to be orthogonal to the tube axis, but if desired the outlet can alternatively be inclined relative to the tube axis. In certain highly desirable embodiments, the outlet is parallel with (by which is meant preferably within 5 degrees) of the surface plane. The supply tube is often cylindrical and advantageously of circular cross section, and especially both internally and externally, though other cross sections can be contemplated such as, for example ovular or ellipsoidal. In many desirable embodiments, the outlet is annular, resulting from the recovery tube being disposed within the supply tube, and in some particularly convenient embodiments, the supply tube has a regular annular outlet. Herein, it is convenient to indicate the cross sectional area of preferred outlets. The outlet preferably has an interior cross section of at least 2 mm$^2$, and more preferably at least 5 mm$^2$ and in some embodiments at least 10 mm$^2$. The interior cross section is normally less than 100 mm$^2$, in many practical embodiments is less than 75 mm$^2$, such as from 25 to 60 mm$^2$. In many suitable probes, the supply tube has an internal diameter of from 5 to 10 mm.

The recovery tube is positioned and oriented to receive through its inlet a fraction of the gas that is expelled through the supply tube outlet. Provided that the inlet is in the proximity of the supply tube outlet and within the boundary of the probe's skirt, the spatial disposition of said inlet and outlet is at the discretion of the probe maker. In some embodiments which encourage the gas to sweep across the target surface, the supply tube outlet faces at least partly towards, and is separated from, the recovery tube inlet, with the target surface in between, the gas thereby flowing laterally across the surface. The separation is desirably not more than 5 mm. Advantageously, in such embodiments, the inlet and outlet also at least partially faces each other, such as by inclining them relative to their respective recovery and supply tubes.

In another and preferred set of embodiments, the inlet faces the surface and advantageously is parallel with it, within for example 5 degrees. In this second set of embodiments, the inlet is likewise parallel with the supply tube outlet. In this second set of embodiments, the gas egressing from the supply tube commonly undergoes laminar flow proximate to the surface. In this second set, the recovery tube inlet can be adjacent to and spaced from the supply tube outlet, if desired, but it is especially convenient if the recovery inlet is positioned within the outlet. The recovery tube is desirably cylindrical and advantageously of circular cross section, especially internally or both externally and internally. Desirably the recovery tube shares a common axis with or has an axis parallel with the supply tube and/or the skirt. In very preferred embodiments, all three are co-axial and in the most preferred embodiments, the skirt is an extension of the supply tube and the recovery tube is located within the supply tube, and especially conveniently is co-axial.

The recovery tube inlet often has a cross sectional area that is from 2 to 50%, and particularly from 3 to 20%, of the available cross sectional area of the supply tube outlet. The inlet desirably has an internal cross section equivalent to having a diameter of at least 0.3 mm (at least about 0.08 mm$^2$) and often equivalent to at least 0.5 mm (at least about 0.12 mm$^2$). The internal cross section of the inlet is often equivalent to a diameter of at least 0.8 mm (0.5 mm$^2$ and in many embodiments equivalent to a diameter not greater than 1.5 mm (about 1.75 mm$^2$), especially when the recovery tube is disposed within the supply tube. The recovery tube can comprise a pipe or alternatively comprise a microporous solid, optionally fibrous with its fibres extending axially or comprising a powder.

Cross sections of the tube outlet and inlet herein are calculated on the basis of being orthogonal to the tube axis. If they are inclined to the axis then the cross section areas are given by A/sine θ where A is the orthogonal surface area and θ is the angle of inclination to the tube axis.

Whilst it is particularly suitable for the probe to be held in the hand and placed on the target surface, it can be contemplated in some circumstances for the probe to carry a modification to enable it to be detachably affixed to the surface for example human skin. By way of example, if the probe is sampling from an arm or leg, the probe could be strapped thereto, possibly with elasticated straps attached to opposite sides of the probe and extending longitudinally and around the arm or leg.

The invention sampler device employs a pressurised gas supply that is uncontaminated. This is conveniently provided by a gas that has been generated free from contaminants such as particulates or suspended droplets or has been purified, filtered or decontaminated and, if necessary, dried. Desirably, the gas comprises nitrogen, especially when the surface forms part of a living mammal, such as human skin. Air that has been dried, filtered and decontaminated can be considered as an alternative, as can carbon dioxide, particularly when the surface does not constitute mammalian skin. Inert gasses, though technically feasible are not usually employed, and especially in the context of human skin.

The gas is desirably caused to flow through the outlet at a rate of from 1 to 20 liters/minute and preferably 1 to 4 liters per minute, or alternatively at a linear velocity of at least 3 cm/sec and particularly at least 5 cm/sec. The maximum preferred gas velocity often depends on the nature of the proximate surface. For hard, inanimate surfaces, a maximum velocity of up to 200 cm/sec can be contemplated, but for an animate surface such as skin, it is preferable not to exceed 20 cm/sec, and a velocity of not above 10 cm/sec can be particularly suitable. Such a flow rate for skin is particularly suited to evaporating and volatilising substances on skin or similar surfaces within a reasonable timescale and enabling them to be collected conveniently.

The gas supply most conveniently comprises an adjustable pressure regulator, intermediate between the gas storage vessel and the probe. The gas pressure is commonly regulated at between 0.1 to 1 bar above atmospheric pressure and particular is regulated to enable the gas to flow through the supply tube outlet at a velocity and/or at a volume rate within the range disclosed hereinbefore.

In many embodiments, the gas is supplied at or around ambient temperature, such as in the range of 20 to 25° C. However, if desired, taking into account the nature of the target surface and the likely substance to be volatilised, the gas can be heated by a heater in the gas supply line intermediate between the gas storage vessel and the probe, most conveniently employing electrical heating elements. For animate surfaces, the temperature is advantageously not higher than about 40 to 45° C., but for inanimate surfaces, higher temperatures can be contemplated, for example up to about 100° C. for many thermoplastics and even higher for metals or ceramics.

The recovery tube is connected in fluid-tight communication to the collector which commonly comprises an absorbent or adsorbent trap filled with a gas permeable solid that is chemically compatible with and capable of absorbing or adsorbing the volatilised substance. It will be recognised that the choice of solid can vary depending on the nature of volatilised substance, and can be the subject of prior testing or can often be identified from published literature. Suitable solids can include inorganic materials such as molecular sieves, including for example, zeolites, carbon (charcoal), alumina, and/or silica, which can be in the form of powder or granules or compressed to a permeable tablet, or organic materials such as macroreticular resins, cotton, or cellulose in the form often of massed fibre or absorbent sheet, e.g. cotton wool or blotting paper. The collector can preferably comprise a cartridge that can be either replaced as an entity or emptied and refilled for each individual sample. As an alternative, if the probe is employed near an analytical apparatus such as a gas analyser, the collector can comprise a connector for gaseous communication from the recovery tube to such apparatus.

In one convenient set of embodiments, the collector comprises a carbon resin which is physically capable of extracting a range of volatilisable substances from a gas flow. The substances can be desorbed-conveniently therefrom for analysis by a conventional desorption process at elevated temperature, such as at about 200° C.

It is often convenient in operation to collect the volatilised substances from at least 20 mls of the carrier gas flowing through the collector, such as up to 100 mls and preferably up to 50 mls.

The probe tube walls, at or in the vicinity of the respective outlet or inlet are advantageously made from any solid that is readily formed and, for multiple use, decontaminated. Especially for single use, a mouldable thermoplastic such as polyethylene, polypropylene, polyethylene terephthalate or polycarbonate can be contemplated. However, for multiple use, it is preferable to employ passivated stainless steel or alloys based on nickel, chromium or titanium that are strong, can be formed into tubes with a narrow internal diameter and decontaminated and disinfected. Glass tubes can be contemplated for use in sampling from inanimate surfaces.

The probe can, if desired, be unitary or advantageously can comprise two pieces in gas-tight assembly, in the upper piece the supply tube being attachable to the gas supply and the recovery tube to the collector and the lower piece constituting the supply tube outlet, the recovery tube inlet and the skirt. A two piece assembly permits decontamination/sterilisation of the lower piece, which comes into contact with the target surface or its replacement should it become damaged, or the selection of outlet/inlet of different cross section areas or dispositions, such as for sampling from different target surface or different volatilisable substances or, if desired, the employment of disposable lower pieces.

The sampler according to the present invention is well suited to collecting samples of volatilisable substances which may be exogenously or endogenously generated, such as substances within, inter alia, the following classes, including classes including substances that are observable on a mammalian body or other surface, such as in particular skin, possibly following a compound transformation by a bacterial population or by fungi or otherwise:

Steroids including 17-oxo-5α-androsten-3β-yl sulfate (dehydroepiandrosterone), 17-oxo-5α-androstan-3α-yl sulfate (Androsterone sulfate), 5α-androst-16-en-3-one (androstenone), 5,16-Androstadien-3β-ol (androstadienol), 4,16-androstadien-3-one (androstadienone), 4,16-androstadien-3α-ol, 5α-androst-2-en-17-one, Androsta-3,5-dien-17-one, Androsta-2,4-dien-17-one, Isomeric-dien-17-one, and cholesterol;

Low molecular weight, volatilisable fatty acids including Isovaleric acid, acetic acid, propionic acid, isobutyric acid, butyric acid, caproic acid, 3-methyl-2-hexenoic acid, 3-methyl-2-pentenoic acid, 3-methylhexanoic acid, 3-hydroxy-3-methylhexanoic acid;

Thiols including 3-methyl-3-sulfanylhexan-1-ol, 2-methyl-3-sulfanylbutan-1-ol, 3-methyl-3-sulfanylbutan-1-ol, 3-sulfanylhexan-1-ol, 3-sulfanylpentan-1-ol.

Ketones such as acetone and 2-Piperidone.

Aldehydes such as (E)-2-nonenal, decanal, hexanal, nonanal, undecanal;

Esters such as Dodecanoic acid-methyl ester, hexanoic acid methyl ester, methyl 9-methyltetradecanoate and Aliphatic/aromatic hydrocarbons such as dodecane, naphthalene, nonane.

Other substances readily detectable by the invention sampler include fragrances, many compounds of which are alcohols, esters, aldehydes or amines.

The invention sampler is conveniently used by opening the gas supply to a desired pressure, to supply gas through the supply tube of the probe at a desired flow rate, bringing the probe skirt into contact with a desired region of the target surface, such as skin, and maintaining contact and flow rate until a desired volume of gas has passed through the collector.

The invention sampler can be used conveniently to collect samples of volatilisable substances from a very small region of the target surface, including, for example pores or glands in skin, such as the apocrine gland, the eccrine gland, the apoeccrine gland and/or the sebaceous gland.

By virtue of its size and often its light weight, the invention sample is of potential value in obtaining samples of volatilisable compounds from the underarm and areas of the body that are comparatively difficult to access using bulky sampling devices, including for example behind the ears, between toes, within the buccal cavity, and by virtue of its small contact area to samples from hair follicles or from localised areas of the body suffering from inflammation, eczema or other skin conditions, wounds or tumours.

In a further aspect of the present invention, there is provided a method for determining the efficacy of a treatment, be it therapeutic or non-therapeutic, which induces-or alters the extent to which a volatilisable substance is present in a region of a target surface of a body. In such a method, a treatment is administered to a body having that surface, for example to the surface itself, and the sampler takes a sample of said substance before and after the treatment or on at least two occasions after the treatment, the samples are compared so that the efficacy of the treatment and/or the speed of the treatment can be ascertained.

Without being restrictive to such uses, the invention sampler is of particular benefit in sampling substances from individual glands or clusters of glands in human skin, depending on the size of the gland mouth and the spacing (density) of the glands, which varies over the body. Thus, for example, the sampler can determine the effectiveness of a non-therapeutic deodorant or deodorant ingredient applied topically to human skin over a period of time, for example by comparison with a treatment-free site or placebo and can track the variation in a reference volatile substance or substances that are generated from individual glands, or because of the gland density a cluster of glands. Thus, for example, within the underarm vault, eccrine glands typically have a gland mouth of about 0.045 mm and are spaced apart by about 0.5 mm, but at a lower density elsewhere. Skin bacteria transform non-odorous substances exuded through various glands into more volatile substances having, to many humans, an unpleasant odour, such as, inter alia, low molecular weight carboxylic acids and sulphides. The sampler can track the rate of generation of such malodorous compounds over time and thus plot the extent to which and for how long any proposed non-therapeutic deodorant treatment is effective, including for example use of known deodorants such as triclosan, chlorhexidine, aluminium and/or zirconium salts, glyceryl stearate and poly(methylenebiguanide), and mixtures of any two or more thereof, or other compounds of unknown capability.

Likewise, apocrine glands and their associated hair follicles are commonly spaced at about 2 mm apart, so that the invention sampler is well suited to taking samples from individual glands.

Likewise, the sampler can be used to track the generation of volatilisable substances following topical administration, ingestion, or injection of a drug or medicine, or even the ingestion of food or drink. Substances, the tracking of which can be contemplated include nicotine, cannbinoids such as Δ(9)tetrahydrocannbinol, cocaine HCl, ecgonine methyl ester, benzoylecgonine, methadone, Gamma-hydroxybutyric acid, methamphetamine, amphetamine, and benzodiazepines.

Having summarised and described the invention in general terms, specific embodiments will now be described in more detail with reference to the accompanying Figures in which.

Figure 1:
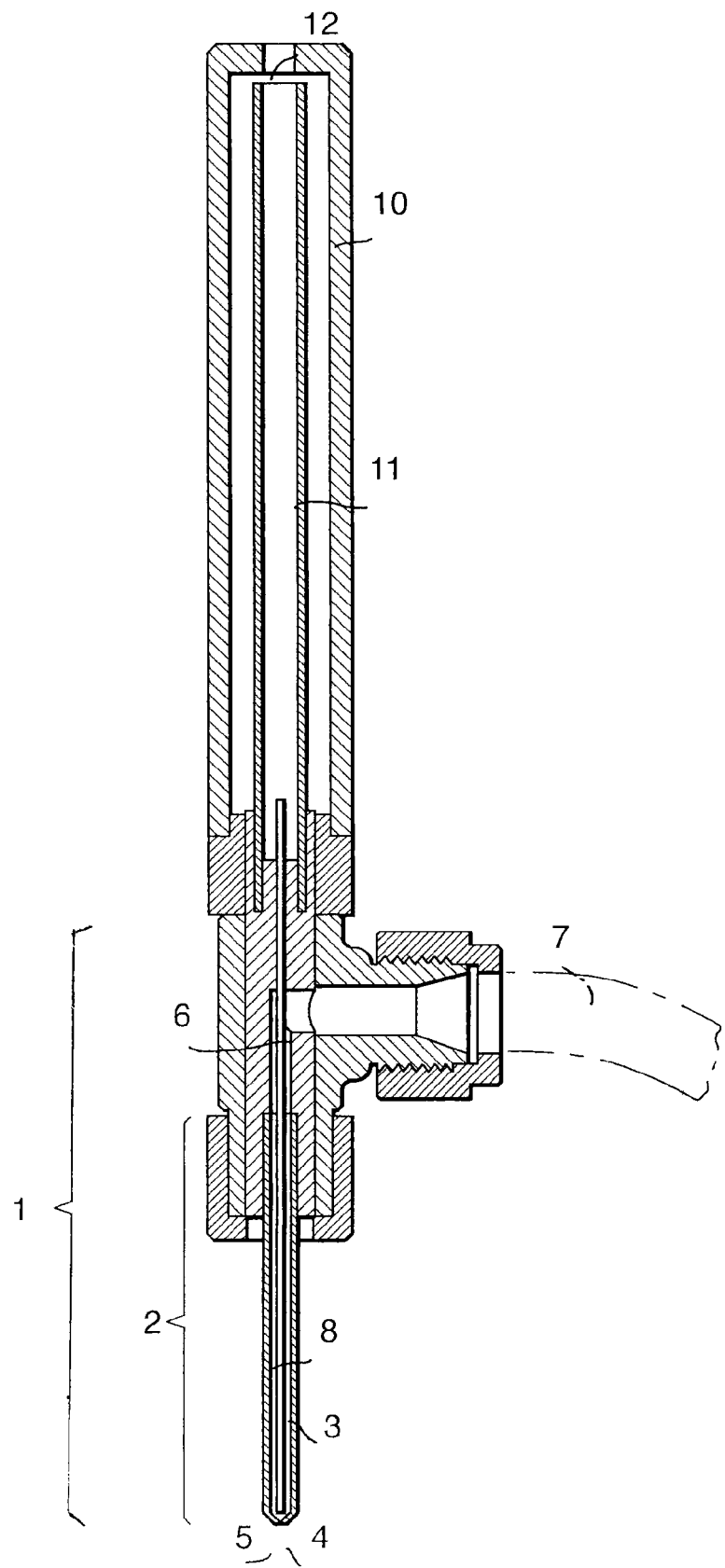
FIG. 1 shows the probe and collector in schematic axial section view.
Figure 2:
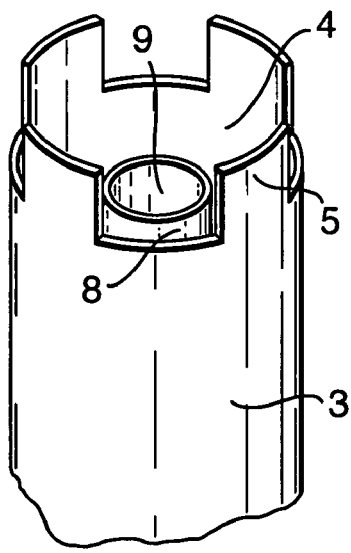
FIG. 2 is a ¾ view of the tip of the probe of FIG. 1.
Figure 3:
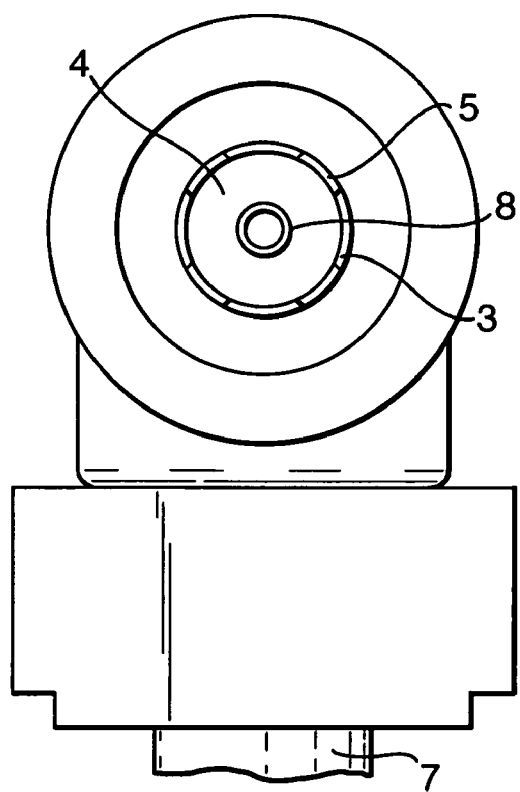
FIG. 3 shows an underside plan view of the device of FIG. 1.

In the embodiment described in relation to FIGS. 1 to 3, the sampling device comprises a probe (1) having a detatchable tip section (2) which comprises an outer supply tube (3) made from "Silco"™ stainless steel, terminating at one end in an annular outlet (4) located within a castellated skirt (5) of internal diameter 3 mm and castellations of depth 0.5 mm and at its other end is in fluid communication via a port (6) with a gas supply tube (7) from a pressurized nitrogen gas supply (not illustrated). The supply tube (3) surrounds and is concentric with an inner capillary recovery tube (8) having a circular inlet (9) of diameter 0.5 mm parallel-with the tips of the skirt castellations at a height of 1 mm. The recovery tube (8) extends through an airtight PTFE insert (10) into an absorptive trap (11) containing a permeable bed of proprietary sampling adsorbent material absorptive resin and having a remote gas outlet (12).

In operation, the gas supply is turned on to a regulated pressure, and the castellated skirt (5) is brought into contact squarely with a surface such as over an apocrine gland in human skin (not illustrated). The nitrogen flows through the annular outlet (4) into contact with the skin, volatilising substances from and close to the surface with a fraction of it flowing out between the castellations, preventing ingress of contamination, and the remainder flowing into the recovery tube (8) bearing the volatilised substances. The gas the flows into the recovery trap (11) where the bed of adsorbent resin extracts the volatilised substances, and the stripped gas flows out through trap outlet (12). In a subsequent operation, the volatilised substances are desorbed-from the bed of adsorbent resin at elevated temperature and carried on a non-reactive gas into a gas chromatograph, or to a detector optimised to monitor a specific volatile component from the skin, for example an ion mobility or differential mobility spectrometer, selected and set up in accordance with the manufacturer's instructions to monitor the target component.

Figure 4:
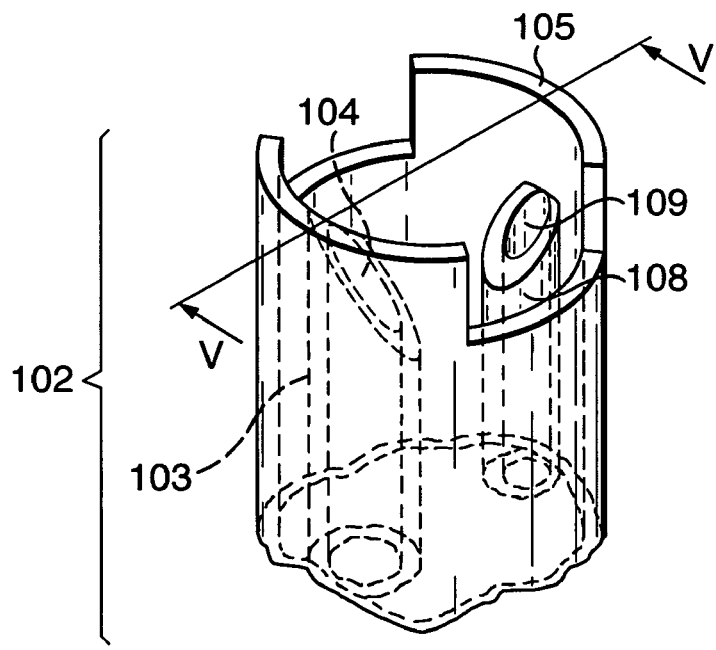
FIG. 4 shows a ¾ view of the tip of an alternative probe.
Figure 5:
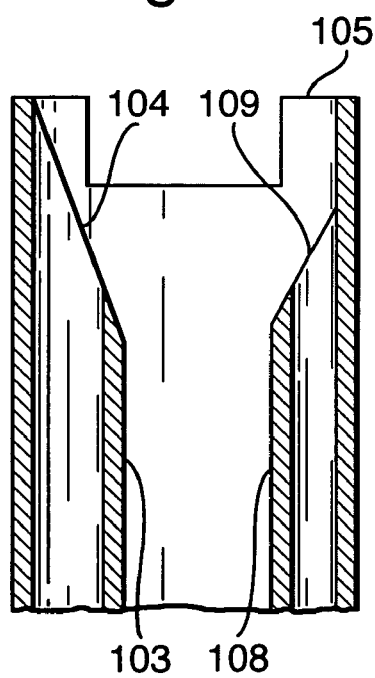
FIG. 5 shows an axial cross sectional view of the probe tip of FIG. 4.
Figure 6:
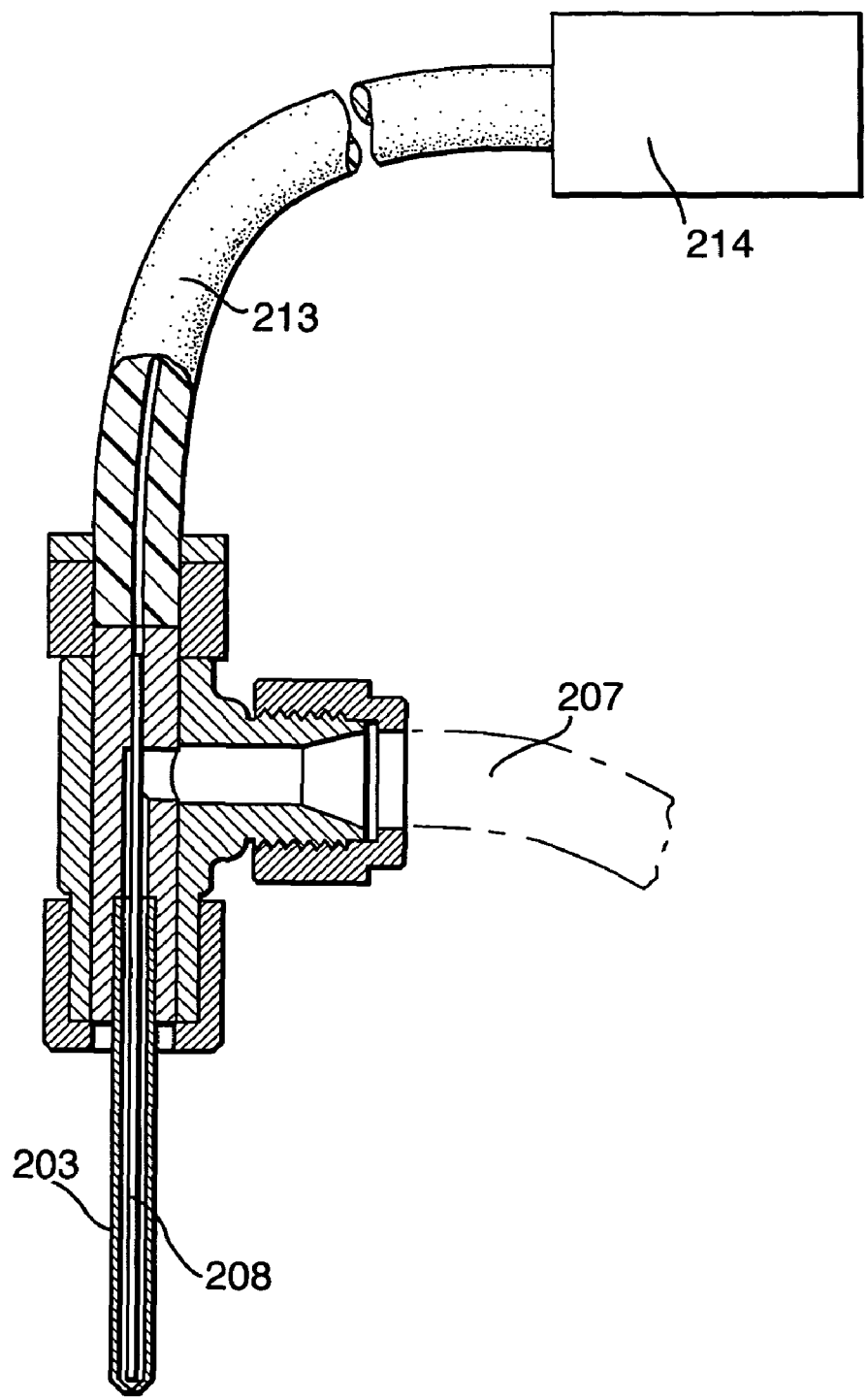
FIG. 6 shows a schematic view of an alternative embodiment

In an alternative embodiment shown in FIGS. 4 and 5, the device comprises a modification of the device of FIG. 1, in which supply tube (103) and recovery tube (108) and disposed on diametrically opposite sides within the castellated skirt (105) of internal diameter 6mm of the probe tip section (102). The supply tube outlet (104) of internal diameter 3 mm and the recovery tube inlet (109) of internal diameter 0.5 mm are each inclined at an angle of about 30 degrees to their respective parallel axes and face each other.

In a further embodiment comprising a modification of the device of FIG. 1, the recovery tube (208) does not lead into the trap for the volatilised substances of FIG. 1, but instead is in gas tight connection with line (213) leading into a gas chromatograph (214). In this embodiment, analysis of the substances volatilised from the target surface is instantaneous.

EXAMPLE 1

In this Example, the sampler described with reference to FIGS. 1 to 3 was maintained in contact with the skin in the axilla vault of a Caucasian male for 5 min employing nitrogen as the carrier gas at a flow rate of 7.5 cms/sec. The sampled volatiles were recovered from the adsorbent trap by thermal desorption using a Unity Thermal Desorption unit interfaced to Varian gas chromatography mass spectrometer fitted with a 30 m 5% phenyl/95% methyl capillary column with an internal diameter of 0.25 mm and a film thickness of 0.5 µm. The resultant trace can be compared with standard reference compounds to identify the presence of cyclobutylamine and nonanal.

By repeating the sampling at intervals of 30 minutes, the change in concentration of those substances are monitored.

Likewise, the effect of a deodorant can be monitored by a method of first washing the underarm to which no deodorant has been applied for at least 24 hours thoroughly with a soap solution, rinsing it and drying it, and taking a sample as described in Example 1. Immediately, thereafter, a deodorant is applied such as triclosan (0.1%) in an ethanolic carrier liquid (60% ethanol, 40% water) formed into an aerosol composition (87% w/w propane/butane/isobutane, 13% ethanolic composition) and measurements taken at 1 hour and 5 hour interval thereafter. The method is repeated on the other axilla to which no deodorant is applied.

The invention claimed is:

1. A method of sampling a volatilisable substance from a region of a body surface which comprises:
    bringing a probe into contact with the body surface, the probe comprising:
        a supply tube in fluid communication with a pressurised gas supply and having an outlet,
        a recovery tube in communication with a collector and having an inlet adjacent to said supply tube outlet, and either
        (1) a skirt of varied depth that extends beneath and surrounds the recovery tube inlet, the skirt also extending beneath and surrounding the supply tube outlet, or
        (2) the supply tube including a skirt portion of varied depth that extends beneath and surrounds the recovery tube inlet;
    directing under pressure a gas through the supply tube outlet onto said surface of the body, thereby volatilizing substances on the body surface, and
    recovering a fraction of the gas through the recovery tube inlet, the varied depth of the skirt or skirt portion allowing the remainder of the gas to flow outwardly beneath the skirt or skirt portion.

2. A method in accordance with claim 1 in which the gas is delivered at a flow rate of from 0.5 to 10 liters/minute though the supply tube outlet.

3. A method in accordance with claim 2 in which the gas is delivered at a flow rate of from 1 to 5 liters/minute though the supply tube outlet.

4. A method in accordance with claim 1 in which the gas is delivery through the supply tube outlet at a velocity of from 0.02 to 0.2 m/sec.

5. A method in accordance with claim 1 in which the surface comprises skin.

6. A method in accordance with claim 5 in which the probe is positioned over an apocrine, eccrine or sebaceous gland or cluster of glands.

7. A method of determining the efficacy of a therapeutic or non-therapeutic treatment administered to a body, which comprises: sampling a volatilisable substance from a region of a body surface before and after, and/or at two or more intervals after, administration of the treatment to the body surface and comparing the samplings; wherein the samplings are obtained by a procedure that comprises:
    bringing a probe into contact with the body surface, the probe comprising:
        a supply tube in fluid communication with a pressurised gas supply and having an outlet,
        a recovery tube in communication with a collector and having an inlet adjacent to said supply tube outlet, and either
        (1) a skirt of varied depth that extends beneath and surrounds the recovery tube inlet, the skirt also extending beneath and surrounding the supply tube outlet, or
        (2) the supply tube including a skirt portion of varied depth that extends beneath and surrounds the recovery tube inlet; and
    directing under pressure a gas through the supply tube outlet onto said surface of the body, thereby volatilizing substances on the body surface, and
    recovering a fraction of the gas through the recovery tube inlet, the varied depth of the skirt or skirt portion allowing the remainder of the gas to flow outwardly beneath the skirt or skirt portion.

8. A method in accordance with claim 7 in which the treatment comprises administering a deodorant active to human skin.

* * * * *